US011795820B2

United States Patent
Jones et al.

(10) Patent No.: US 11,795,820 B2
(45) Date of Patent: *Oct. 24, 2023

(54) DUAL PUMP REVERSE FLOW THROUGH PHASE BEHAVIOR MEASUREMENTS WITH A FORMATION TESTER

(71) Applicant: Halliburton Energy Services, Inc., Houston, TX (US)

(72) Inventors: Christopher Michael Jones, Katy, TX (US); Darren George Gascooke, Houston, TX (US); Anthony Herman Van Zuilekom, Houston, TX (US); Marcus Ray Hudson, Pearland, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/090,360

(22) Filed: Dec. 28, 2022

(65) Prior Publication Data
US 2023/0137185 A1 May 4, 2023

Related U.S. Application Data

(63) Continuation of application No. 17/133,482, filed on Dec. 23, 2020, now Pat. No. 11,572,786.

(51) Int. Cl.
*E21B 49/10* (2006.01)
*G01N 33/28* (2006.01)

(52) U.S. Cl.
CPC ......... *E21B 49/10* (2013.01); *G01N 33/2823* (2013.01)

(58) Field of Classification Search
CPC .... E21B 49/081; E21B 49/0875; E21B 49/10; G01N 33/2823
See application file for complete search history.

(56) References Cited

U.S. PATENT DOCUMENTS

| | | | | |
|---|---|---|---|---|
| 4,936,139 A | * | 6/1990 | Zimmerman | E21B 49/08 73/152.41 |
| 5,934,374 A | * | 8/1999 | Hrametz | E21B 49/10 166/264 |

(Continued)

FOREIGN PATENT DOCUMENTS

WO     2014110255 A1     7/2014

OTHER PUBLICATIONS

Office Action Summary for U.S. Appl. No. 17/133,482 dated Aug. 24, 2022.

(Continued)

*Primary Examiner* — Jennifer H Gay
(74) *Attorney, Agent, or Firm* — John Wustenberg; C. Tumey Law Group PLLC (57) ABSTRACT

A downhole PVT tool for performing in-situ formation fluid phase behavior characterizations in a wellbore using pressure, volume, and temperature (PVT) measurements of the formation fluid while continuing to pump the formation fluids. The disclosed downhole PVT tool includes an intake mandrel and utilizes two individual pumps to split the formation fluid to perform PVT measurements during the fluid pump out. The downhole PVT tool, two-pump configuration permits a first pump to be used to pump formation fluid along a first flowpath and a second pump to be used to pump formation fluid along a second flowpath, with one or more sensors deployed along one of the flowpaths to perform fluid and/or gas phase behavior measurements to determine one or more properties of the formation fluid in-situ. The first pump may be utilized in the phase behavior analysis while the second pump simultaneously continues flow-through pumping of the formation fluid.

19 Claims, 3 Drawing Sheets

(56) References Cited

U.S. PATENT DOCUMENTS

| | | | |
|---|---|---|---|
| 6,301,959 B1* | 10/2001 | Hrametz | E21B 49/10 73/152.01 |
| 7,249,009 B2 | 7/2007 | Ferworn et al. | |
| 7,346,460 B2 | 3/2008 | DiFoggio et al. | |
| 7,458,252 B2* | 12/2008 | Freemark | E21B 49/10 73/64.45 |
| 7,461,547 B2 | 12/2008 | Terabayashi et al. | |
| 7,526,953 B2* | 5/2009 | Goodwin | E21B 47/10 73/152.28 |
| 7,788,972 B2 | 9/2010 | Terabayashi et al. | |
| 7,920,970 B2 | 4/2011 | Zue et al. | |
| 8,109,157 B2 | 2/2012 | Kanayama et al. | |
| 8,162,052 B2 | 4/2012 | Goodwin et al. | |
| 8,210,260 B2* | 7/2012 | Milkovisch | E21B 49/008 166/264 |
| 8,256,283 B2 | 9/2012 | Terabayashi et al. | |
| 8,397,561 B2 | 3/2013 | Yamate et al. | |
| 8,434,357 B2* | 5/2013 | Hsu | E21B 47/114 73/152.24 |
| 8,528,396 B2* | 9/2013 | Wu | E21B 49/082 73/152.55 |
| 8,555,968 B2* | 10/2013 | Zazovsky | E21B 49/008 166/264 |
| 8,813,554 B2* | 8/2014 | Fujisawa | E21B 49/081 73/152.27 |
| 8,925,379 B2 | 1/2015 | Yamate et al. | |
| 9,016,369 B2 | 4/2015 | Atkinson et al. | |
| 9,057,250 B2* | 6/2015 | Zazovsky | E21B 49/10 |
| 9,284,838 B2* | 3/2016 | Cernosek | E21B 49/081 |
| 9,303,509 B2* | 4/2016 | Milkovisch | E21B 49/008 |
| 9,322,267 B2* | 4/2016 | Pop | E21B 49/10 |
| 9,670,775 B2 | 6/2017 | Tjhang et al. | |
| 9,671,211 B2 | 6/2017 | Gao et al. | |
| 11,384,637 B2* | 7/2022 | Hsu | E21B 49/08 |
| 11,572,786 B2* | 2/2023 | Jones | E21B 49/10 |
| 2006/0117842 A1* | 6/2006 | Ramakrishnan | E21B 49/10 73/152.55 |
| 2006/0243033 A1* | 11/2006 | Freemark | E21B 49/10 73/64.45 |
| 2007/0079962 A1* | 4/2007 | Zazovsky | E21B 49/08 166/264 |
| 2007/0119244 A1* | 5/2007 | Goodwin | E21B 47/10 73/152.28 |
| 2008/0073078 A1* | 3/2008 | Sherwood | E21B 49/10 166/264 |
| 2010/0155061 A1* | 6/2010 | Zazovsky | E21B 49/008 166/264 |
| 2010/0175873 A1* | 7/2010 | Milkovisch | G01N 33/0009 166/264 |
| 2011/0042071 A1* | 2/2011 | Hsu | E21B 47/114 166/250.01 |
| 2012/0222852 A1* | 9/2012 | Pelletier | E21B 49/10 417/282 |
| 2012/0304757 A1* | 12/2012 | Fujisawa | E21B 49/081 73/152.28 |
| 2013/0046473 A1* | 2/2013 | Zhang | E21B 47/113 702/6 |
| 2013/0075088 A1* | 3/2013 | Milkovisch | E21B 49/008 166/264 |
| 2014/0196532 A1* | 7/2014 | Bullock | E21B 49/08 73/152.24 |
| 2016/0130940 A1* | 5/2016 | Hsu | E21B 49/10 702/11 |
| 2018/0175873 A1 | 4/2018 | Milkovische et al. | |
| 2019/0353632 A1 | 11/2019 | Pelletier et al. | |
| 2020/0400017 A1* | 12/2020 | Olapade | E21B 49/081 |
| 2022/0195871 A1* | 6/2022 | Jones | E21B 49/10 |

OTHER PUBLICATIONS

Notice of Allowance for U.S. Appl. No. 17/133,482 dated Dec. 6, 2022.

Search Report issued for International Patent Application No. PCT/US2021/067039, dated Sep. 2021, 12 pages.

* cited by examiner

DUAL PUMP REVERSE FLOW THROUGH PHASE BEHAVIOR MEASUREMENTS WITH A FORMATION TESTER

CROSS-REFERENCED TO RELATED APPLICATIONS

The present application is a continuation of U.S. application Ser. No. 17/133,482 filed on Dec. 23, 2020, which is incorporated herein by reference in their entirety for all purposes.

TECHNICAL FIELD

The disclosure relates, in general, to wellbore fluid measurements, and more specifically to tools and methods for performing downhole phase behavior measurements of formation fluids in a wellbore.

BACKGROUND

During the drilling and completion of oil and gas wells, it may be necessary to engage in ancillary operations, such as evaluating the production capabilities of formations intersected by the wellbore. For example, after a well or well interval has been drilled, zones of interest are often tested to determine various formation properties or formation fluid characteristics, or to gather fluid samples. Examples of formation fluid information which can be obtained include formation fluid identification, fluid type, fluid quality, formation permeability, formation temperature, formation pressure, bubblepoint and formation pressure gradient. These tests are performed in order to determine whether commercial exploitation of the intersected formations is viable and how to optimize production. The acquisition of accurate data from the wellbore is important to the optimization of hydrocarbon wells. This wellbore data can be used to determine the location and quality of hydrocarbon reserves, whether the reserves can be produced through the wellbore, and for well control during drilling operations.

One particular area of interest is the study of pressure, volume, and temperature (PVT) changes on formation fluid, and specifically how changes in PVT impact phase behavior of the formation fluid. In such case, it is sometimes desirable to obtain a sample of formation fluid that may be substantially free of contaminants such as mud filtrate or other formation debris entrained in the formation fluid sample or otherwise to understand the degree of contaminants and their impact on PVT and phase behavior. In the prior art, downhole PVT tools for such analysis include a main flowline or flowpath for the formation fluid and a bypass flowline or flowpath. A single pump directs formation fluid along the main flowline and a valve downstream of the pump may be used to close off the main flowline and direct the pumped formation fluid into the bypass flowline where the formation fluid is isolated for testing. Upon isolation of this formation fluid sample, the bypass flowline is closed off and formation fluid flow can be resumed along the main flowline. One drawback to such prior art downhole PVT tools is that the altered flowpath may negatively impact the formation fluid sample for phase change evaluation purposes. For example, the turbulence from an altered flowpath may result in a fluid sample with more formation debris entrained in the fluid and may also alter the phase characteristics of the formation fluid sample. Another drawback is that isolation activities limit continued flow-through activities along the main flowline.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

The downhole PVT tools and methods disclosed herein relate to pressure, volume, and temperature (PVT) measurements of formation fluid, and specifically relate to the study of phase behavior of the formation fluid at various PVT measurements while pumping the fluid in a subsurface wellbore. In accordance with disclosed embodiments, the downhole PVT tool permits fluid phase behavior analysis using PVT measurements to be performed while continuing to pump formation fluid through the downhole PVT tool along a main flow line or flowpath without the need to suspend flow along the main flow line. In some embodiments, this can result in a formation fluid sample that is less contaminated than samples obtained by prior art downhole PVT tools. Regardless, this can also allow continued flow-through of formation fluid along the main flowline even as phase behavior of the formation fluid is being analyzed. The downhole PVT tools and methods disclosed herein utilize two individual pumps to isolate a formation fluid sample. A first pump is utilized to direct formation fluid along a first flowpath while a second pump is used to independently direct formation fluid along a second flowpath. In some embodiments, the first pump may draw formation fluid from the second flowpath as the formation fluid continues to flow along the second flowpath. The formation fluid drawn by the first pump from the second flowpath is directed to a first flowpath for isolation and analysis. The first pump can be utilized to pressurize the isolated formation fluid sample along the first flowpath while formation fluid continues to flow uninterrupted along the second flowpath. Once the formation fluid sample is isolated along the first flowpath, various PVT measurements can be obtained, and as stated, the formation fluid sample in the first flowpath may be pressurized utilizing the first pump. Thereafter, pressure on the formation fluid sample may be bled off by allowing the isolated formation fluid sample to flow to the wellbore annulus or merge back with the second flowpath. In some embodiments, the first pump may be reversed and operated to pump the formation fluid sample into the wellbore annulus or into the second flowpath. In some embodiments, a 4-way high pressure valve may be utilized to accomplish the pump reversal activities that are needed for performing the measurements, although other implementation and/or methods of pump reversals can also be employed. In some embodiments, a metered pump can be used, for example, for fine control during PVT measurements, including for example, during depressurization.

As introduced above, the disclosed downhole PVT tools and methods are designed to perform in-situ phase behavior characterization based on PVT measurements, including for example, density measurements as a function of pressure in the downhole environment. Example fluidic characterization approaches may include, but are not limited to, for example probing gas to liquid volume measurements as a function of pressure. In various implementations of the downhole PVT tools, constant composition expansion experiments can be performed for phase behavior analysis, for example, for performing fluid fraction, compressibility, viscosity, and gas-oil-ratio (GOR) measurement. In addition, the downhole PVT tools and methods can be configured to perform gas phase only measurements to measure, for example, hydrogen sulfide ($H_2S$) in a subsurface wellbore.

Disclosed herein are embodiments of a downhole PVT tool and methods for performing in-situ phase behavior measurements in a wellbore. In one or more embodiments, the downhole PVT tool has a two pump configuration, where a first pump is used to pump fluid along a first flowpath and a second pump is used pump fluid along a second flowpath, with one or more sensors deployed along one of the flowpaths to perform fluid and/or gas phase behavior measurements to determine one or more properties of the formation fluid in-situ.

Figure 1:
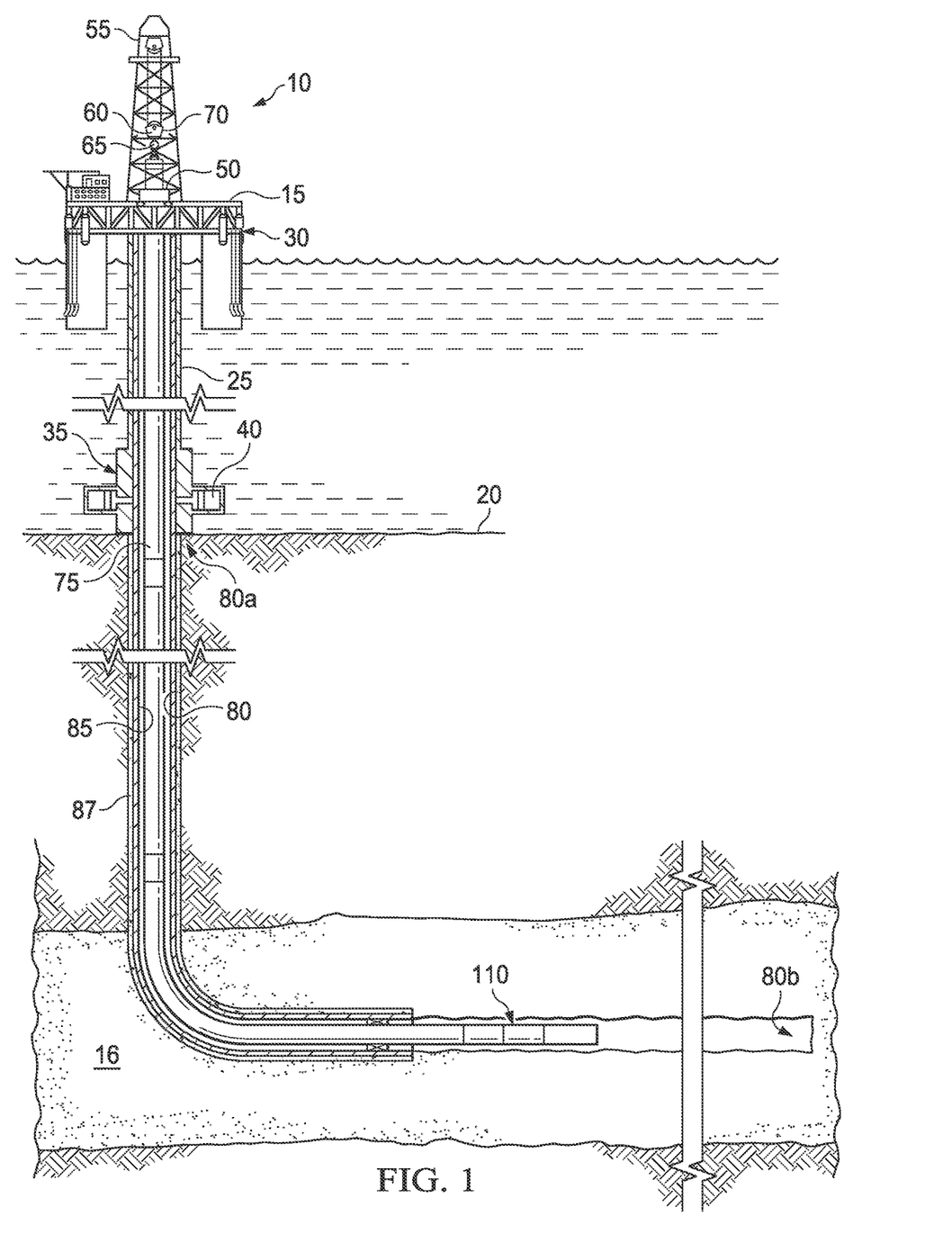
FIG. 1 is a schematic illustration of an offshore oil and gas platform operably coupled to a subsurface wellbore, according to one or more embodiments of the present disclosure.

Referring to FIG. 1, in an embodiment, an offshore oil and gas rig is schematically illustrated and generally referred to by the reference numeral 10. In an embodiment, the offshore oil and gas rig 10 includes a semi-submersible platform 15 that is positioned over a submerged oil and gas formation 16 located below a sea floor 20. A subsea conduit 25 extends from a deck 30 of the platform 15 to a subsea wellhead installation 35. One or more pressure control devices 40, such as, for example, blowout preventers (BOPs), and/or other equipment associated with drilling or producing a wellbore may be provided at the subsea wellhead installation 35 or elsewhere in the system. The platform 15 may also include a hoisting apparatus 50, a derrick 55, a travel block 60, a hook 65, and a swivel 70, which components are together operable for raising and lowering a conveyance string 75. The conveyance string 75 may be, include, or be part of, for example, a casing, a drill string, a completion string, a work string, a pipe joint, coiled tubing, production tubing, other types of pipe or tubing strings, and/or other types of conveyance strings, such as wireline, slickline, and/or the like. The platform 15 may also include a kelly, a rotary table, a top drive unit, and/or other equipment associated with the rotation and/or translation of the conveyance string 75. A wellbore 80 extends from an upper end or surface end 80a adjacent the subsea wellhead installation 35, through the various earth strata, including the submerged oil and gas formation 16, to a lower or terminal end 80b. At least a portion of the wellbore 80 may include a casing 85 cemented therein by cement 87. The conveyance string 75 is, includes, or is operably coupled to a downhole PVT tool 110 so as to position the downhole PVT tool 110 within wellbore 80 at a subterranean location. Although downhole PVT tool 110 is illustrated in FIG. 1 in a horizontal wellbore 80, wellbore 80, and its orientation, are for illustrative purposed only and downhole PVT tool 110 can function equally well in vertical wellbores of other deviated wellbores.

Figure 2:
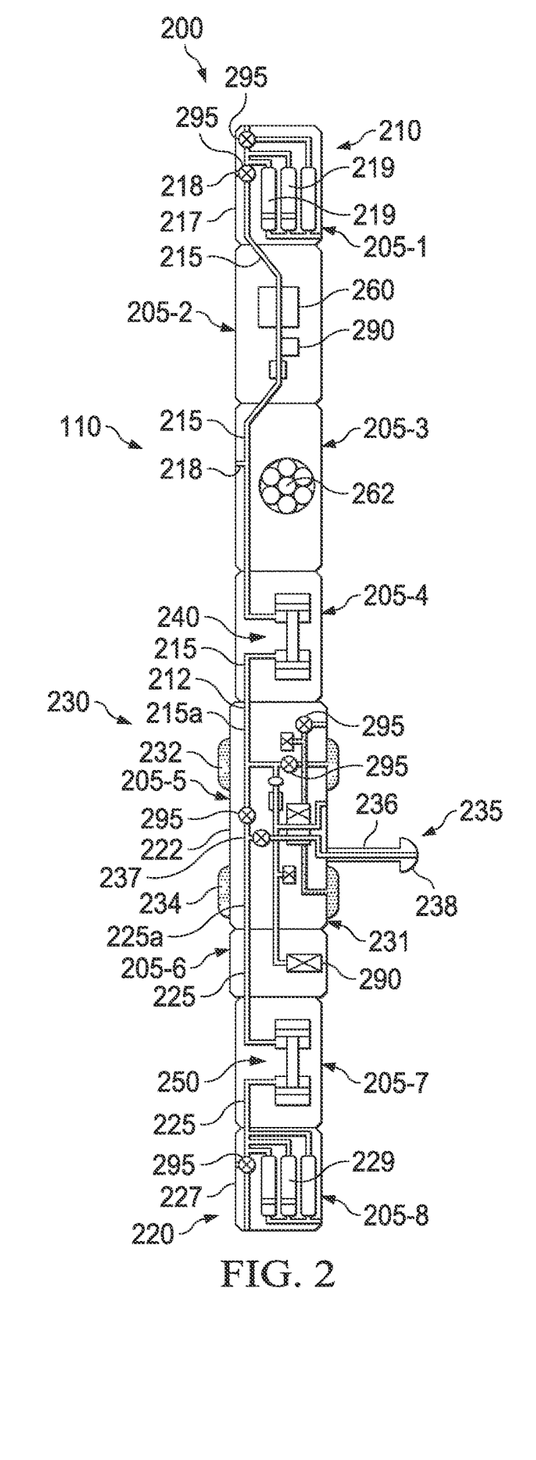
FIG. 2 is a cross-sectional view of a pressure, volume, and temperature (PVT) tool for downhole testing within a wellbore illustrated in FIG. 1, according to one or more embodiments of the present disclosure.

Referring to FIG. 2, with continuing reference to FIG. 1, in an embodiment, the downhole PVT tool 110 is shown as downhole PVT tool 200. Downhole PVT tool 200 is operable to perform phase behavior measurements in-situ on formation fluids. In one or more embodiments, the downhole PVT tool 200 has a first tool end 210, which can be referred to as the upper end, and a second tool end 220, which can be referred to as the lower end. It will be appreciated that in one or more embodiments, downhole PVT tool 200 is generally positioned within a wellbore 80 so that first tool end 210 extends towards the surface end 80a of wellbore 80, while second tool end 220 extends towards the terminal end 80b of wellbore 80. Moreover, whether wellbore 80 is substantially vertical or deviated, in one or more embodiments, first tool end 210 will generally be positioned above, or otherwise have a higher elevation than, second tool end 220 such that gas entrained within formation fluid captured within downhole PVT tool 200 will have a tendency to migrate towards first tool end 210. In one or more embodiments, the downhole PVT tool 200 includes an intake mandrel 230 formed of an intake mandrel body 231. In one or more embodiments, intake mandrel 230 may be an isolation packer with a first packer element 232 spaced apart from a second packer element 234 along the intake mandrel body 231. Although not limited to a particular type of packer, in one or more embodiments, intake mandrel 230 can be a pad-based packer, a focused packer or an unfocused packer. In any event, intake mandrel 230 also includes at least one port mechanism 235 disposed along the intake mandrel body 231. Where intake mandrel 230 is a packer, port mechanism 235 may be positioned along intake mandrel body 231 between the first and second packer elements 232 and 234, respectively. In one or more embodiments, port mechanism 235 may be an aperture formed along intake mandrel body 231, while in other embodiments, port mechanism 235 may be a suction arm or probe 236 that extends from intake mandrel body 231 to engage an adjacent wall of wellbore 80 (see FIG. 1). Where port mechanism 235 is a suction arm 236, suction arm 236 may include a pad 238 that bears against the wall of wellbore 80.

In one or more embodiments, the downhole PVT tool 200 includes a first flowpath 215 formed within one or more tool segments 205-1 to 205-8, collectively referred to as "segments 205" and which segments 205 include intake mandrel 230. As used herein, to the extent a "flowpath" is formed in a component of downhole PVT tool 200, it may also be referred to as or otherwise considered a flowline. In any event, the first flowpath 215 extends from a first end 212 fluidically coupled to the port mechanism 235 (the first end 212 begins at segment 205-5) to a second end 217 (the second end 217 ends at segment 205-1). The downhole PVT tool 200 may include at least one exit valve 218 disposed along the first flowpath 215, and in one or more embodiments, it has two or more exit valves 218. Downhole PVT tool 200 also includes a first pump 240 fluidically coupled to the first flowpath 215. In one or more embodiments, first pump 240 is disposed along first flowpath 215 between exit valve 218 and the first end 212.

As illustrated in FIG. 2, in one or more embodiments, a second flowpath 225 is formed within one or more tool segments 205, with second flowpath 225 extending from a first end 222 to a second end 227, the first end 222 of the second flowpath 225 fluidically coupled to the port mechanism 235. As illustrated, the first end 222 begins at segment 205-5, i.e., intake mandrel 230. In the illustrated embodiment, the second end 227 terminates at segment 205-8. Downhole PVT tool 200 includes a second pump 250 fluidically coupled to the second flowpath 225. In one or more embodiments, second pump 250 is disposed along second flowpath 225 between the two ends 222 and 227.

While first and second flowpaths 215, 225 are shown spaced apart from one another in different segments 205 of downhole PVT tool 200, in other embodiments, first and second flowpaths 215, 225 may be formed in the same segments 205 so long as the first and second flowpaths 215, 225 remain separate from one another except as described herein adjacent intake mechanism 235.

As described above, when downhole PVT tool 200 is deployed, first tool end 210 will tend to be oriented above second tool end 220. For this reason, in one or more embodiments, first flowpath 215 is spaced apart from second flowpath 225, and in particular, first flowpath 215 extends towards first tool end 210 while second flowpath 215 extends towards second tool end 320. As such, phase behavior analysis can take advantage of the natural tendency of gas within the formation fluid to migrate towards the second end 217 of first flowpath 215, i.e., end 210 of downhole PVT tool 200 that is closest to the surface end 80a of wellbore 80.

Downhole PVT tool 200 may also include at least one primary sensor system 260 disposed along the first flowpath 215 between the first pump 240 and the second end 217 of the first flowpath 215. Although not limited to a particular type of sensor, in one or more embodiments, primary sensor system 260 may include any one or more of a pressure sensor, a temperature sensor, a density sensor or a densitometer, a flow rate sensor, composition sensor, an optical sensor, a capacitance sensor, a resistivity sensor, a sonic sensor, an ultrasonic sensor, a chromatometer, and a microfluidic sensor, and the like.

In one or more embodiments, the downhole PVT tool 200 may further include at least one sample chamber disposed along one or both flowpaths 215, 225. In the illustrated embodiment, multiple sample chambers 219 are shown near the first tool end 210, while a second sample chamber 220 is shown near the second tool end 220. In one or more embodiments, the downhole PVT tool 200 also includes one or more temperature sensors 290 disposed along one or both flowpaths 215, 225. Each flowpath 215, 225 may further include valves 295 within one or more tool segments 205. In one or more embodiments, the downhole PVT tool 200 may also include an optical sensor 262, which, among other things, may be used to determine phase change or the concentration of contaminants in the formation fluid sample, although it will be understood that other sensors may be used for this purpose. In various embodiments, a fluid property analyzer is electrically coupled to one of the sensors 260 or 262.

In one or more embodiments, at least a portion 215a of first flowpath 215 is defined within intake mandrel 230 and at least a portion 225a of second flowpath 225 is defined within intake mandrel 230 extending from port mechanism 235. In some embodiments portion 215a of first flowpath 215 and portion 225a of second flowpath 225a may be separately formed within intake mandrel 230, while in other embodiments, portion 215a of first flowpath 215 and portion 225a of second flowpath 225 may intersect one another, while in yet other embodiments, portion 215a of first flowpath 215 and portion 225a of second flowpath 225 may be the same. Thus, in some embodiments, the initial flowpath from the port mechanism 235 may have a junction 237 at which point the first flowpath 215 extends in a first direction (such as towards first tool end 210) and the second flowpath 225 extends in a second direction (such as towards second tool end 220). In any event, the junction 237 occurs along the flowpath between the port mechanism 235 and the pumps 240, 250. In the illustrated embodiment, a portion 215b, 225b of the flowpaths 215, 225 converge or share a common path from port mechanism 235 to junction 237, at which point flowpaths 215, 225 diverge.

Depending on their configuration as set forth above, at least one flowpath 215, 225 begins at port mechanism 235. Where first and second flowpaths 215, 225 do not intersect or converge or share a common path within intake mandrel 230, intake mandrel 230 may include two port mechanisms 235 (see FIG. 3) where portion 215a of first flowpath 215 is fluidically coupled to one port mechanism 235 and portion 225a of second flowpath 225 is fluidically coupled to a separate port mechanism 235. Where a port mechanism 235 includes a suction arm 236, then the relevant flowpath(s) extends through the suction arm 236. Where a port mechanism 235 includes a pad 238, then the relevant flowpath(s) begins at the pad 238.

Figure 3:
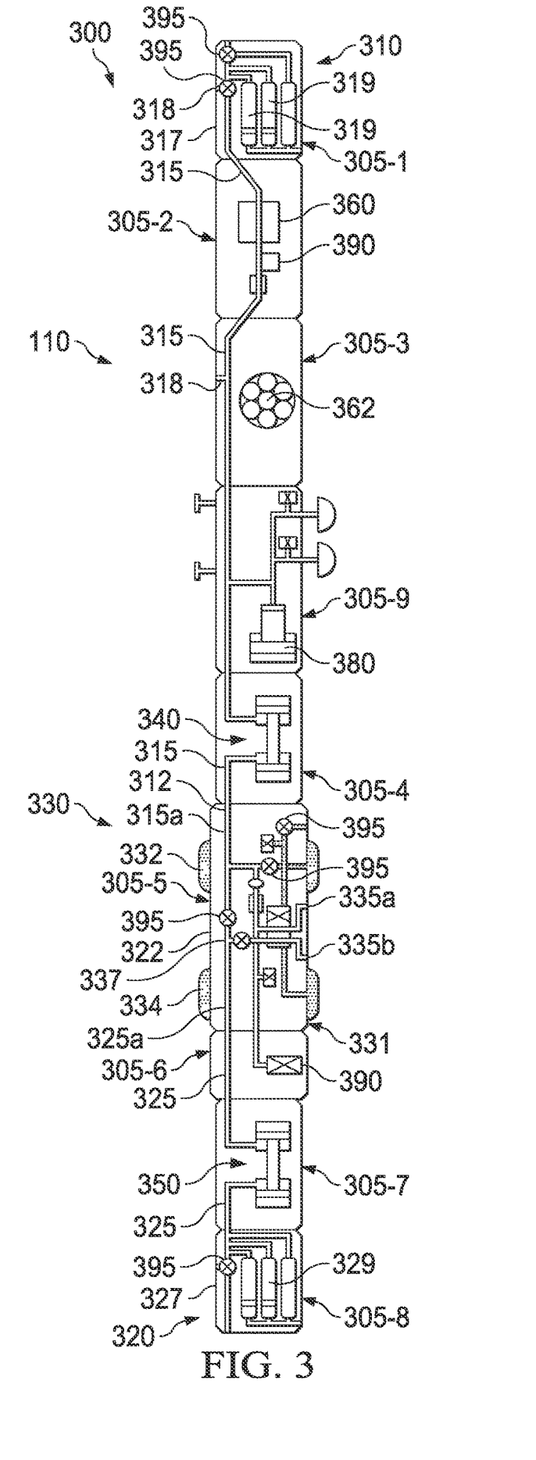
FIG. 3 is a cross-sectional view of another embodiment of a downhole PVT tool of FIG. 1, according to one or more embodiments of the present disclosure.

Referring to FIG. 3, downhole PVT tool 110 is shown as downhole PVT tool 300, in accordance with one or more embodiments of the present disclosure. Downhole PVT tool 300 is operable to perform phase behavior measurements in-situ on formation fluids. Although downhole PVT tool 300 is similar to the downhole PVT tool 200 and includes a first pump 340 and a second pump 350, downhole PVT tool 300 further includes a piston pump 380. In one or more embodiments, piston pump 380 can be configured as a metered pump for fine pressure control during phase behavior tests, such as during, for example, depressurization.

As illustrated in FIG. 3, in accordance with one or more embodiments, downhole PVT tool 300 has a first tool end 310, which can be referred to as the upper end, and a second tool end 320, which can be referred to as the lower end. It will be appreciated that in one or more embodiments, downhole PVT tool 300 is generally positioned within a wellbore 80 so that first tool end 310 extends towards the surface end 80a of wellbore 80, while second tool end 320 extends towards the terminal end 80b of wellbore 80 (see FIG. 1). Moreover, whether wellbore 80 is substantially vertical or deviated, in one or more embodiments, first tool end 310 is generally positioned above, or otherwise has a higher elevation than, second tool end 320 such that gas entrained within formation fluid captured within downhole PVT tool 300 will have a tendency to migrate towards first tool end 310. In one or more embodiments, the downhole PVT tool 300 includes an intake mandrel 330 formed of an intake mandrel body 331. In one or more embodiments, intake mandrel 330 may be an isolation packer with a first packer element 332 spaced apart from a second packer element 334 along the intake mandrel body 331 Although intake mandrel 330 is shown as a packer, it need not be, and persons of skill in the art will appreciate that intake mandrel 330 may be any tool component that can be utilized to establish fluid communication with the wellbore annulus or the formation. In any event, intake mandrel 330 includes a port mechanism 335 disposed along intake mandrel body 331. Where intake mandrel 330 is a packer, port mechanism 335 may be positioned along intake mandrel body 331 between the first and second packer elements 332 and 334, respectively. In the illustrated embodiment, a first port mechanism 335a and a separate second port mechanism 335b are illustrated, although first and second port mechanism 335a, 335b could be combined into a single port mechanism 335 such as is described with respect to FIG. 2.

In one or more embodiments, the downhole PVT tool 300 includes a first flowpath 315 formed within one or more tool segments 305-1 to 305-9, collectively referred to as "segments 305" and which segments 305 include intake mandrel 230. Although illustrated as discreet components that make up downhole PVT tool 300, in one or more embodiments, tool segments 305 may be integrally formed into a single piece downhole PVT tool. The first flowpath 315 extends from a first end 312 fluidically coupled to the port mechanism 335a (the first end 312 begins at segment 305-5) to a second end 317 (the second end 317 ends at segment 305-1). The downhole PVT tool 300 may include at least one exit valve 318 disposed along the first flowpath 315, and in one or more embodiments, it has at least two exit valves 318. Exit valves 318 may be in fluid communication with the exterior of downhole PVT tool 300 or with other components of the downhole PVT tool 300, such as expansion chambers or the like. Downhole PVT tool 300 also includes a first pump 340 fluidically coupled to the first flowpath 315. In one more embodiments, first pump 340 is disposed along first flowpath 315 between exit valve 318 and the first end 312. In one or more embodiments, first pump 340 is a variable rate pump to allow the flow rate of formation fluid moving along first flowpath 315 to be varied during investigation of the phase response. Furthermore, first pump 340 is a reversible pump, allowing the direction of flow along first flowpath 315 to be reversed as described herein.

As illustrated in FIG. 3, in one or more embodiments, a second flowpath 325 is formed within one or more tool segments 305, with the second flowpath 325 extending from a first end 322 fluidically coupled to the port mechanism 335b to a second end 327. As illustrated, the first end 322 begins at segment 305-5, i.e. intake mandrel 330. In the illustrated embodiment, the second end 327 terminates at segment 305-8. Thus, the first flowpath 315 generally extends from intake mandrel 330 towards the upper end 310 of downhole PVT tool 300 and the second flowpath 325 generally extends in a direction opposite from the first flowpath 315, namely towards the lower end 320 of downhole PVT tool 300. Downhole PVT tool 300 includes a second pump 350 fluidically coupled to the second flowpath 325. In one or more embodiments, second pump 350 is disposed along second flowpath 325 between the two ends 322 and 327. Second pump 350 may be a reversible pump, such as first pump 340, or a single direction pump. Likewise, second pump 350 may be a variable rate pump or a constant speed pump since it will be appreciated that unlike first pump 340 and first flowpath 315, second pump 350 and second flowpath 325 are not being utilized to investigate phase characteristics of the formation fluid as occurs with respect to first flowpath 325.

Downhole PVT tool 300 may also include at least one primary sensor system 360 disposed along the first flowpath 315 between the first pump 340 and the second end 317 of the first flowpath 315. In one or more embodiments, primary sensor system 360 includes at least a pressure sensor. Although not limited to any further particular type of sensor, primary sensor system 360 may further include one or more of a temperature sensor, a density sensor or a densitometer, a flow rate sensor, composition sensor, an optical sensor, a capacitance sensor, a resistivity sensor, a sonic sensor, an ultrasonic sensor, a chromatometer, and a microfluidic sensor, and the like.

Downhole PVT tool 300 may further include sample chambers 319 and 320 disposed along one or both flow paths 315, 325. In the illustrated embodiment, multiple sample chambers 319 are disposed near the first tool end 310 while a sample chamber 320 is disposed near the second tool end 320. In one or more embodiments, the downhole PVT tool 300 may also include one or more additional sensors 390, such as temperature sensors and/or pressure sensors, within one or more tool segments 305. Further, the downhole PVT tool 300 may include an optical sensor 360 disposed along first flowpath 315. In various embodiments, a fluid property analyzer is electrically coupled to one of the sensors 360 or 362.

As illustrated in FIGS. 2 and 3, the downhole PVT tools 200 and 300 each have two separate pumps, where each pump is disposed to move formation fluid along different flowpaths, and which flowpaths, in one or more embodiments, may extend in opposite directions along the axial length of the downhole PVT tool. By splitting formation fluid flow along separate flowpaths, the flow direction between two points along one flowpath can be reversed while fluid flow along the other flowpath may continue uninterrupted. In this regard, the pump rates along the separate flowpaths may be different. For example, flow along a first flowpath may be varied in order to investigate phase response of the formation fluid to changes in physical conditions. In this regard, the first pump may be used to pressurize or "pump up" the formation fluid sample pressure from a first pressure to a second pressure that is higher than the first pressure, and thereafter, the first pump may be reversed to depressurize, bleed off or otherwise "pump out" the formation fluid sample. In one or more embodiments, a pump rate can be varied more than ten or more times between an open section of a flowpath, i.e., the second flowpath, and a closed section of a flowpath, i.e., the first flowpath, in order to substantially continue the pump out during fluid phase measurements. Using at least one fluid measurement sensor and preferably two or more fluid measurement sensors, fluid properties along the first flowpath may be monitored during pump up and also during pump out. In one or more embodiments, fluid properties to be measured include, but not limited to density, viscosity, temperature, pressure, capacitance, compressibility, sonic/ultrasonic sensors including speed of sound measurements, composition including but not limited to that measured by optical measurements or microfluidic measurements, or chromatographic measurements, as described with respect to FIGS. 2 and 3.

In one or more embodiments, liquid height measurements may also be performed during the pump out of the first flowpath with either multiple fluid sensing measurements from different sensors along one of the flowpaths (in any of the first and second flowpaths 215, 225, 315, or 325) or with distributed sensing measurements along any of the first and second flowpaths 215, 225, 315, or 325. Alternatively, sonic/ultrasonic measurements may be made along any of the flowpaths 215, 225, 315, or 325 to determine liquid height. Such a measurement is most easily made in a single tool section, e.g., any of segments 205 and 305, but may be made in multiple sections. In one or more embodiments, phase changes such as bubble point or asphaltene precipitation point may be directly measured as the point of inflection for any of the fluid measurement sensors, however, optical sensors, such as sensor 260 or 360, are particularly sensitive to these phase changes. Density sensors are also sensitive to bubble point phase changes however less so for asphaltene precipitation phase changes. Using multiple sensors or magnitude readings of the sensors, phase change types may be derived. Compositional changes as a function of pressure may also be measured with compositional sensors for specific fluid phases in which those sensors, e.g., sensors 260, 270, 360, or 370, are in contact. The fluid is also phase separated such that gas phase measurements may be performed, in accordance with one or more embodiments disclosed herein. In other embodiments, measurements may be taken along the first flowpath during pressurization and then during controlled depressurization in order to better characterize the phase behavior of the formation fluid, all while simultaneously continuing to pump formation fluid along the second flowpath.

Based on the downhole PVT tools 200 and 300 described herein, or any variation in the configuration based on the downhole PVT tools 200 and 300, PVT fluid measurements and characterization of phase behavior of a formation fluid can be performed without a bypass flowpath. As discussed above, the use of multiple individual pumps and flowpaths tied into a single probe/packer along separate flowpaths can allow reversal of at least one of those pumps to measure phase behavior without suspending or interfering with formation fluid flow along a separate flowpath.

Figure 4:
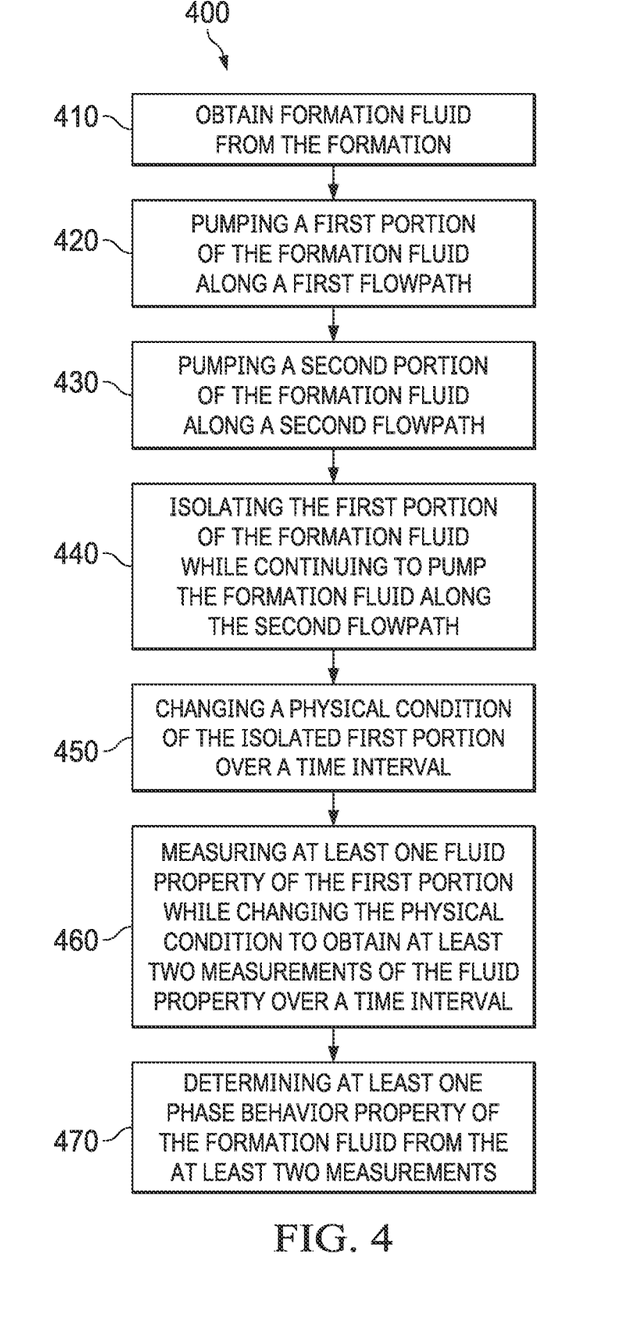
FIG. 4 is a flow diagram of a method for performing in-situ wellbore phase behavior analysis of formation fluid.

Referring to FIG. 4, a downhole method 400 for performing in-situ phase behavior characterization of formation fluid is illustrated. In a first step 410, the method includes obtaining formation fluid from a sampling location along a wellbore. In some embodiments, the wellbore may be at a depth of 100 meters or more, while in other embodiments, the wellbore may be at a depth of 1000 meters or more, while in other embodiments, the wellbore may be at a depth of 2000 meters or more. In each case, it will be appreciated that the formation fluid pressure at the depth of the wellbore is significantly greater than sea level atmospheric pressure. Conducting in-situ phase behavior analysis of the isolated formation fluid sample permits more accurate understanding of phase response to actual conditions at the sampling location than would be the case for samples retrieved and analyzed at the surface. In any event, in one or more embodiments, the formation fluid may be obtained by drawing formation fluid from the formation. As described above, a probe or pad may be utilized to engage a wellbore wall at a sampling location within the formation, and a pump may be activated to create a negative pressure at the junction of the pad or probe with the wellbore wall, thereby causing the formation fluid to be drawn from the formation and into a downhole PVT tool as described herein. In this regard, a downhole PVT tool may be positioned in the wellbore adjacent a zone of interest in formation. Thereafter, a probe or pad may be extended from the downhole PVT tool to engage the wellbore wall and form a suction coupling with the wellbore wall. In other embodiments, the formation fluid may be drawn from the annulus surrounding the downhole PVT tool. In such cases, an isolation packer may be activated to isolate a sampling location along the annulus, and the fluid may be drawn from the annulus at the isolated sampling location.

As the formation fluid is drawn into or otherwise obtained by the downhole PVT tool, in step 420, a first portion of the formation fluid is pumped along a first flowpath, i.e., the first flowpath 215 or 315. Relatedly, at step 430, a second portion of the formation fluid is pumped along a second flowpath, i.e., the second flowpath 225 or 325. In one embodiment, the formation fluid may initially be pumped along a single flowpath, such as when it is drawn in to the tool, and thereafter, the single flowpath may diverge into a first flowpath and a second flowpath, such that formation fluid passing along the first flowpath represents the first portion of the formation fluid and formation fluid passing along the second flowpath represents the second portion of the formation fluid. In this regard, a first pump is used to pump the first portion along the first flowpath and a second pump is used to pump the second portion along the second flowpath. Where the flowpaths initially are converged, the second pump may be utilized to initiate formation fluid flow by generating a negative pressure in the single flowpath to draw the formation fluid into the downhole PVT tool and along the second flowpath as the second portion of the formation fluid. After formation fluid flow is initiated, the first pump may be utilized to draw the first portion from the initiated formation fluid flow. In such case, both pumps may be operated simultaneously.

In other embodiments, the first pump is utilized to draw formation fluid from the formation (or annulus, as the case may be) directly into the first flowpath and the second pump is utilized to draw formation fluid from the formation (or annulus, as the case may be) directly into the second flowpath, such that the first portion of the formation fluid and the second portion of the formation fluid are never comingled. Again, both pumps may be operated simultaneously.

Regardless, as to whether the flowpaths are separate or comingled, the two separate pumps permit simultaneous pumping of the first portion of the formation fluid along a first flowpath and pumping the second portion of the formation fluid along a second flowpath separate from the first flowpath. In one or more embodiments, the first portion of the formation fluid is pumped at a first flowrate and the second portion of the formation fluid is pumped at a second flowrate different than the first flowrate. In some embodiments, the flow rates produced by the two individual pumps can vary more than ten times between the two pumps.

In one or more embodiments where the first and second flowpaths extend in substantially opposite axial directions in the downhole PVT tool, the first portion of the formation fluid is pumped from a sampling location, i.e., the formation fluid intake location, in a first axial direction such as upstream towards the surface end of the wellbore, and the second portion of the formation fluid is pumped from the sampling location in a second axial direction second axial direction such as downstream towards the terminal end of the wellbore. Thus, for each flowpath, the formation fluid is initially pumped from a first end of the flowpath towards a second end of the flowpath. In the case of the first flowpath, a valve may be open at the end of the first flowpath to allow the formation fluid to exit the first flowpath through the valve prior to isolating a formation fluid sample as described below.

At step 440, the first portion of the formation fluid is isolated within the first flowpath while the second portion of the formation fluid along the second flowpath continues to be pumped. This step of the operation is possible because of the use of two individual pumps 240 and 250. In one or more embodiments, the valve described above may be closed so that the first flowpath forms a chamber as pump 240 is operated to fill the chamber.

At step 450, the method 400 includes changing a physical condition of the isolated first portion of the formation fluid. In one or more embodiments, this change may be implemented over a discrete time interval from a time (t1) to a time (t2). In one or more embodiments, the physical condition being changed can be any of pressure, volume, temperature, viscosity, etc. Regardless of the physical condition, the change may be to increase or decrease the physical condition. For example, the change may be to increase or decrease pressure, volume or temperature. In one or more embodiments, changing the physical condition includes changing the fluid pressure of the first fluid portion. In one or more embodiments, changing the fluid pressure is accomplished by altering the volume of the first flowpath. In some embodiments, changing the fluid pressure is accomplished with the first pump by continuing to operate the pump to increase pressure on the first portion of the formation fluid, while in other embodiments, changing the fluid pressure is accomplished with the first pump by reversing the direction of the pump and fluid flow and operating the pump to decrease pressure on the first portion of the formation fluid. In one or more embodiments, changing the physical condition includes increasing the pressure on the first fluid portion over the time interval. In one or more embodiments, changing the physical condition includes decreasing the pressure on the first fluid portion over the time interval. This may be accomplished by pumping the first portion of the formation fluid along the first flowpath in a second direction opposite the first direction, and in particular pumping the first portion along the first flowpath from the second end of the first flowpath towards the first end of the first flowpath. Although not limited to a particular time interval, in some embodiments, the time interval can be from about 1 second to about 10 minutes, from about 10 second to about 1 minutes, from about 1 second to about 1 hour, from about 1 minute to about 24 hours, inclusive of any ranges of time interval between 1 second and 24 hours. Regardless of the time interval, in one or more embodiments, particularly where the formation fluid sample in the first flowpath is drawn from formation fluid flowing along the second flowpath, it is desirable to allow flow-through along the second flowpath for a period of time to minimize the presence of contaminants in the formation fluid sample, seeking as contaminant-free sample as possible.

In step 460, at least one fluid property of the first portion of the formation fluid is measured. In one or more embodiments, the fluid property may be measured before and after a physical property of the first portion of the formation fluid is changed in step 450. Thus, a fluid property measurement may be taken at the first time (t1) and at the second time (t2) to obtain at least two measurements of the fluid property. In other embodiments, the fluid property may be measured as a function of time as the physical condition is changed over the time interval from time (t1) to time (t2). The at least one fluid property measured may include any of pressure, temperature, density, flow rate, composition, optical property, capacitance, resistivity, sonic property, ultrasonic property, chromatographic, and microfluidic, and the like.

Finally, at step 470, the phase behavior of the formation fluid is characterized based on the at least two measurements. In this regard, a phase behavior property may be identified. For example, a phase change pressure point can be identified as pressure is removed from the formation fluid. The phase behavior property of the formation fluid can include any property including, but not limited to fluid fraction, compressibility, viscosity, and gas-oil-ratio (GOR) measurements.

In one or more embodiments of the method 400, pumping the first portion of the formation fluid along the first flowpath includes pumping the first portion along the flowpath in a first direction, e.g., towards segment 205-1 in FIG. 2 (or segment 305-1 in FIG. 3), and then pumping the first portion of the formation fluid along the flowpath in a second direction, e.g., towards segment 205-8 in FIG. 2 (or segment 305-8 in FIG. 3). In one or more embodiments of the method 400, pumping in the first direction includes pumping the first portion along the first flowpath from a first end of the flowpath towards a second end of the flowpath, i.e., from segment 205-5 to segment 205-1 in FIG. 2 (or from segment 305-5 to segment 305-1 in FIG. 3). Likewise, pumping in the second direction includes pumping the first portion along the first flowpath from the second end of the first flowpath towards the first end of the first flowpath, i.e., from segment 205-1 to segment 205-5 in FIG. 2 (or from segment 305-1 to segment 305-5 in FIG. 3).

In one or more embodiments of the method 400, pumping the first portion of the formation fluid along the first flowpath includes pumping the first portion along the first fluid path towards an open first flowpath valve, e.g., exit valve 218 or 318, disposed along the first flowpath. In such instances, the method 400 further includes closing the first flowpath valve to isolate the first portion, continuing to pump the first portion until a predetermined pressure on the first portion is reached, bleeding down the pressure on the first portion, and then, measuring the fluid property as the pressure on the first portion is bled down. In one or more embodiments, bleeding down can include pumping the first portion from the first flowpath.

In one or more embodiments, pumping the first portion from the first flowpath includes pumping the first portion into the wellbore annulus around the downhole PVT tool. In other embodiments, pumping the first portion from the first flowpath includes pumping the first portion to the second flowpath. In some embodiments of the method 400, isolating means closing a valve along the first flowpath. In some embodiments, changing the physical condition of the isolated first portion includes continuing to pump the first portion until a predetermined pressure on the first portion is reached, bleeding down the pressure on the first portion, and measuring the fluid property as the pressure on the first portion is bled down. In such instances, bleeding down may include pumping the first portion from the first flowpath.

In one or more embodiments of the method 400, pumping the first portion and second portion of the formation fluid can include pumping the first portion at a first flowrate and pumping the second portion at a second flowrate different than the first flowrate. In some instances, the first flowrate is higher than the second flowrate. In other instances, the reverse is true. In still yet one or more other embodiments, the second flowrate for pumping the second portion compensates the rate addition of the first flowpath due to the reversal.

While in some embodiments it is desirable to minimize contaminants in the formation fluid sample isolated in the first flowpath, it may be desirable to obtain formation fluid sample data with a variety of samples having different contaminant levels or concentrations, such as a measured amount of mud filtrated per liter of sample. Using contaminated samples with different levels or concentrations of contamination, PVT properties for a hypothetical "contaminant-free" formation fluid sample can be estimated. These PVT properties for the hypothetical "contaminant-free" formation fluid sample can then be utilized to estimate phase behavior of the formation fluid. In yet other embodiments, PVT properties may be measured as a function of contamination concentration of the formation fluid to consider how various properties of the formation fluid are impacted by contamination. Thus, a contaminant concentration and a PVT property of a first formation fluid sample may be measured and compared to a contaminant concentration and the PVT property of a second formation fluid sample with a different concertation. This can permit the estimation of the impact of the concentration on the measured PVT property. Similarly, a contaminant concentration and a physical property of a first formation fluid sample may be measured and compared to a contaminant concentration and the physical property of a second formation fluid sample with a different concertation. This can permit the estimation of the impact of the contaminant concentration on the measured physical property. In other embodiments, a contaminant concentration and a phase behavior property of a first formation fluid sample may be measured and compared to a contaminant concentration and the phase behavior of a second formation fluid sample with a different concertation. This can permit the estimation of the impact of the contaminant concentration on the measured phase behavior property.

In one or more embodiments, the fluid property that can be measured includes one of pressure, temperature, density, flow rate, composition, optical property, capacitance, resistivity, sonic property, ultrasonic property, chromatographic, and microfluidic. In other embodiments, the two measurements can be a pressure measurement. In one or more embodiments, these measurements can be performed at multiple locations along the first flowpath through a distributed measurement system. In one or more embodiments, changing the internal volume of the fluid induces a phase change in the fluid, and a height of free gas above the fluid can be measured after the phase change. In one or more embodiments, at least one phase behavior property that can be determined includes fluid fraction, compressibility, viscosity, and gas-oil-ratio (GOR) measurement.

Thus, a downhole PVT tool for performing in-situ phase behavior measurements in a wellbore has been described. The downhole PVT may include an intake mandrel having an intake mandrel body with a port mechanism disposed along the intake mandrel body; a first flowpath formed within one or more tool segments, the first flowpath having a first end and a second end, with the first end of the first flowpath fluidically coupled to the port mechanism; at least one exit valve disposed along the first flowpath; a first pump fluidically coupled to the first flowpath; a second flowpath formed within one or more tool segments, the second flowpath having a first end and a second end, with the first end of the second flowpath fluidically coupled to the port mechanism; a second pump fluidically coupled to the second flowpath; and at least one primary sensor system disposed along the first flowpath between the second pump and the second end of the first flowpath.

For any of the foregoing embodiments, the downhole PVT tool may include any one of the following elements, alone or in combination with each other:

The downhole PVT tool has a first tool end and a second tool end.

The downhole PVT tool has an isolation packer having a first packer element spaced apart from a second packer element along a packer body with a port disposed along the packer body between the first and second packer elements.

The downhole PVT tool has a first flowpath formed within one or more tool segments.

The first flowpath has a first end and a second end, with the first end of the first flowpath fluidically coupled to the port.

Each tool segment has an exterior surface.

The downhole PVT tool has at least one exit valve disposed along the first flowpath.

The downhole PVT tool has a first pump fluidically coupled to the first flowpath between the exit valve and the first end of the first flowpath.

The downhole PVT tool has a second flowpath formed within one or more tool segments.

The second flowpath has a first end and a second end, with the first end of the second flowpath fluidically coupled to the port.

The downhole PVT tool has a second pump fluidically coupled to the second flowpath between the two ends of the second flowpath.

The downhole PVT tool has at least one primary sensor system disposed along the first flowpath between the second pump and the second end of the first flowpath.

The downhole PVT tool has at least one secondary sensor system disposed along the second flowpath.

The first pump is a reversible pump.

At least one of the pumps is a variable speed pump.

The first flowpath extends from the isolation packer towards the first tool end.

The second flowpath extends from the isolation packer towards the second tool end.

At least one primary sensor system includes a sensor selected from the group consisting of a pressure sensor, a temperature sensor, a density sensor, a flow rate sensor, composition sensor, an optical sensor, a capacitance sensor, a resistivity sensor, a sonic sensor, an ultrasonic sensor, a chromatometer, and microfluidic sensor.

The downhole PVT tool has a fluid property analyzer electrically coupled to the at least one primary sensor.

Relatedly, a method for performing downhole, in-situ phase behavior measurements of formation fluid collected in a wellbore has been described. Embodiments of the method may include drawing formation fluid from the wellbore; pumping a first portion of the formation fluid along a first flowpath; pumping a second portion of the formation fluid along a second flowpath; isolating the first portion of the formation fluid while continuing pump the second portion of the formation fluid along the second flowpath; changing a physical condition of the isolated first portion over a time interval; measuring at least one fluid property of the first portion while changing the physical condition; obtaining at least two measurements of the fluid property over the time interval; and determining at least one phase behavior property of the formation fluid from the at least two measurements. In other embodiments, the method may include performing downhole phase behavior measurements may include drawing a fluid from a formation through a probe, the probe attached to a first flowpath and a second flowpath; pumping the fluid to the first flowpath via a first pump, the first flowpath having at least one exit valve fluidically connected to the first flowpath; closing the at least one exit valve of the first flowpath, thereby isolating the fluid located in the first flowpath from the wellbore; changing an internal volume of the fluid attached to the first flowpath by actuating the first pump; measuring at least one fluid property at least two different internal volume levels; and determining at least one phase behavior property from the at least one measured fluid property. In yet other embodiments, the method may include obtaining formation fluid from a sampling location in the wellbore; pumping a first portion of the formation fluid along a first flowpath; pumping a second portion of the formation fluid along a second flowpath; isolating the first portion of the formation fluid along the first flowpath while continuing to pump formation fluid along the second flowpath; changing a physical condition of the isolated first portion over a time interval while continuing to pump formation fluid along the second flowpath; measuring at least one fluid property of the first portion while changing the physical condition to obtain at least two measurements of the fluid property over the time interval; and determining at least one phase behavior property of the formation fluid from the at least two measurements. In still yet other embodiments, the method may include engaging the formation with a probe at a sampling location within a wellbore; drawing formation fluid from the formation through the probe; pumping the formation fluid from the probe to a first flowpath via a first pump; isolating the formation fluid located in the first flowpath; increasing pressure on the isolated formation fluid utilizing the first pump and then decreasing the pressure on the isolated formation fluid; simultaneously as the pressure on the isolated formation fluid is increased utilizing the first pump, utilizing a second pump to pump formation fluid from the probe along a second flowpath; measuring at least one fluid property of the formation fluid of the first flowpath over a time interval as the pressure on the formation fluid in the first flowpath is decreased; and determining at least one phase behavior property from the at least one measured fluid property.

For the foregoing embodiments, the method may include any one of the following steps, alone or in combination with each other:

- Changing the physical condition includes changing pressure on the first fluid portion.
- Obtaining formation fluid from a formation at a sampling location comprises drawing formation fluid from the formation.
- Obtaining formation fluid from a formation at a sampling location comprises engaging a wellbore wall with a pad and creating a negative pressure at the surface of the pad to draw formation fluid into a flowpath.
- Obtaining formation fluid from a formation at a sampling location comprises drawing formation fluid from the annulus around a downhole PVT tool.
- Pumping a first portion of the formation fluid along a first flowpath comprises pumping the first portion from the sampling location upstream towards surface; and pumping a second portion of the formation fluid along a second flowpath comprises pumping the second portion from the sampling location downstream towards the wellbore end.
- Pumping a first portion of the formation fluid along a first flowpath comprises pumping the first portion from the sampling location upstream towards surface.
- Pumping a second portion of the formation fluid along a second flowpath comprises pumping the second portion from the sampling location downstream towards the wellbore end.
- Changing the pressure includes altering the volume of the first flowpath.
- Changing the physical condition includes increasing the pressure on the first fluid portion over the time interval, and measuring the fluid property at a first time and a second time.
- Changing the physical condition includes decreasing the pressure on the first fluid portion over the time interval, and measuring the fluid property at a first time and a second time.
- Pumping a first portion of the formation fluid along a first flowpath and simultaneously pumping a second portion of the formation fluid along a second flowpath.
- Pumping the second portion of the formation fluid along the second flowpath is simultaneous with pumping the first portion of the formation fluid along the first flowpath.
- Utilizing a first pump to pump a first portion of the formation fluid along the first flowpath; and utilizing a second pump to pump a second portion of the formation fluid along the second flowpath.
- Pumping the first portion of the formation fluid along the first flowpath includes pumping the first portion along the flowpath in a first direction; and then pumping the first portion of the formation fluid along the flowpath in a second direction.
- Pumping in the first direction includes pumping the first portion along the first flowpath from a first end of the flowpath towards a second end of the flowpath.
- Pumping in the second direction includes pumping the first portion along the first flowpath from the second end of the flowpath towards the first end of the flowpath.
- Pumping the first portion of the formation fluid along the first flowpath includes pumping the first portion along the first fluid path towards an open first flowpath valve disposed along the first flowpath.
- Measuring contaminant concentration and a PVT property of a first formation fluid sample; measuring a contaminant concentration and the PVT property of a second formation fluid sample with a different concertation; and estimating the impact of the contaminant concentration on the measured PVT property.
- The measured PVT property is temperature.
- The measured PVT property is pressure.
- Measuring contaminant concentration and a physical property of a first formation fluid sample; measuring a contaminant concentration and the physical property of a second formation fluid sample with a different concertation; and estimating the impact of the contaminant concentration on the measured physical property.
- Measuring contaminant concentration and a phase behavior property of a first formation fluid sample; measuring a contaminant concentration and the phase behavior property of a second formation fluid sample with a different concertation; and estimating the impact of the contaminant concentration on the measured phase behavior property.
- The method may include closing the first flowpath valve to isolate the first portion.
- The method may include continuing to pump the first portion until a predetermined pressure on the first portion is reached.
- The method may include bleeding down the pressure on the first portion.
- The method may include measuring the fluid property as the pressure on the first portion is bled down.
- Bleeding down includes pumping the first portion from the first flowpath.
- Pumping the first portion from the first flowpath includes pumping the first portion back into the wellbore.
- Pumping the first portion from the first flowpath includes pumping the first portion to the second flowpath.
- Isolating includes closing a valve along the first flowpath.
- Changing the physical condition of the isolated first portion includes continuing to pump the first portion until a predetermined pressure on the first portion is reached; bleeding down the pressure on the first portion; and measuring the fluid property as the pressure on the first portion is bled down.
- Bleeding down includes pumping the first portion from the first flowpath.
- Pumping the first portion and second portion of the formation fluid includes pumping the first portion at a first flowrate and pumping the second portion at a second flowrate different than the first flowrate.
- The first flowrate is higher than the second flowrate.
- The second flowrate for pumping the second portion compensates the rate addition of the first flowpath due to the reversal.
- At least one fluid property measured includes one of pressure, temperature, density, flow rate, composition, optical property, capacitance, resistivity, sonic property, ultrasonic property, chromatographic, and microfluidic.

One of the at least two measurements is a measurement of pressure.

At least one fluid property measured occurs at multiple locations along the first flowpath through a distributed measurement system.

Changing the internal volume induces a phase change in the fluid, and a height of free gas above the fluid is measured after the phase change.

At least one phase behavior property determined is one of fluid fraction, compressibility, viscosity, and gas-oil-ratio (GOR) measurement.

While various embodiments have been illustrated in detail, the disclosure is not limited to the embodiments shown. Modifications and adaptations of the above embodiments may occur to those skilled in the art. Such modifications and adaptations are in the spirit and scope of the disclosure.

What is claimed is:

1. A method for performing downhole in-situ phase behavior measurements of formation fluid collected in a wellbore extending from a surface end to a terminal end, the method comprising:
    obtaining formation fluid from a sampling location in the wellbore;
    pumping a first portion of the formation fluid along a first flowpath;
    pumping a second portion of the formation fluid along a second flowpath, wherein the second flowpath is in an opposite direction from the first flowpath;
    isolating the first portion of the formation fluid along the first flowpath while continuing to pump formation fluid along the second flowpath;
    changing a physical condition of the isolated first portion over a time interval while continuing to pump formation fluid along the second flowpath;
    measuring at least one fluid property of the first portion while changing the physical condition to obtain at least two measurements of the fluid property over the time interval; and
    determining at least one phase behavior property of the formation fluid from the at least two measurements.

2. The method of claim 1, wherein changing the physical condition comprises changing pressure on the first fluid portion.

3. The method of claim 1, wherein the first flowpath extends from an intake mandrel towards a first tool end and the second flowpath extends from the intake mandrel towards a second tool end.

4. The method of claim 1, wherein changing the physical condition comprises increasing the pressure on the first fluid portion over the time interval, and measuring the fluid property at a first time and a second time.

5. The method of claim 1, wherein changing the physical condition comprises decreasing the pressure on the first fluid portion over the time interval, and measuring the fluid property at a first time and a second time.

6. The method of claim 1, wherein pumping the first portion of the formation fluid along the first flowpath comprises pumping the first portion along the flowpath in a first direction; and then pumping the first portion of the formation fluid along the flowpath in a second direction.

7. The method of claim 6, wherein pumping in the first direction comprises pumping the first portion along the first flowpath from a first end of the flowpath towards a second end of the flowpath; and wherein pumping in the second direction comprises pumping the first portion along the first flowpath from the second end of the flowpath towards the first end of the flowpath.

8. The method of claim 1, wherein pumping the first portion of the formation fluid along the first flowpath comprises pumping the first portion along the first fluid path towards an open first flowpath valve disposed along the first flowpath; the method further comprising:
    closing the first flowpath valve to isolate the first portion;
    continuing to pump the first portion until a predetermined pressure on the first portion is reached;
    bleeding down the pressure on the first portion; and
    measuring the fluid property as the pressure on the first portion is bled down.

9. The method of claim 8, wherein bleeding down comprises pumping the first portion from the first flowpath.

10. The method of claim 8, wherein pumping the first portion from the first flowpath comprises pumping the first portion into an annulus within the wellbore.

11. The method of claim 1, wherein changing the physical condition of the isolated first portion comprises continuing to pump the first portion until a predetermined pressure on the first portion is reached; bleeding down the pressure on the first portion; and measuring the fluid property as the pressure on the first portion is bled down.

12. The method of claim 1, wherein determining at least one phase behavior property comprises measuring contaminant concentration and a physical property of a first formation fluid sample; measuring a contaminant concentration and the physical property of a second formation fluid sample with a different concertation; and estimating the impact of the contaminant concentration on the measured physical property.

13. A downhole PVT tool for performing phase behavior measurements in a wellbore, the downhole PVT tool having a first tool end and a second tool end, comprising:
    an intake mandrel having an intake mandrel body with a port mechanism disposed along the intake mandrel body;
    a first flowpath formed within one or more tool segments, the first flowpath having a first end and a second end, with the first end of the first flowpath fluidically coupled to the port mechanism;
    at least one exit valve disposed along the first flowpath;
    a first pump fluidically coupled to the first flowpath, wherein the first pump is a reversible pump;
    a second flowpath formed within one or more tool segments, wherein the second flowpath has a first end and a second end, wherein the first end of the second flowpath is fluidically coupled to the port mechanism, wherein the port mechanism is an arm with a suction pad attached thereto, at least one of the flowpaths extending through the arm to the suction pad, and wherein the second flowpath is in an opposite direction from the first flowpath;
    a second pump fluidically coupled to the second flowpath; and
    at least one primary sensor system disposed along the first flowpath between the second pump and the second end of the first flowpath.

14. The system of claim 13, further comprising:
    at least one secondary sensor system disposed along the second flowpath.

15. The system of claim 13, wherein the first flowpath extends from the intake mandrel towards the first tool end and the second flowpath extends from the intake mandrel towards the second tool end.

16. The system of claim 13, wherein the at least one primary sensor system comprises a sensor selected from the group consisting of a pressure sensor, a temperature sensor, a density sensor, a flow rate sensor, composition sensor, an optical sensor, a capacitance sensor, a resistivity sensor, a sonic sensor, an ultrasonic sensor, a chromatometer, and microfluidic sensor.

17. A method for performing downhole in-situ phase behavior measurements of formation fluid collected in a wellbore extending from a surface end to a terminal end, the method comprising:
- engaging the formation with a probe at a sampling location within a wellbore;
- drawing formation fluid from the formation through the probe;
- pumping the formation fluid from the probe to a first flowpath via a first pump;
- isolating the formation fluid located in the first flowpath;
- increasing pressure on the isolated formation fluid utilizing the first pump and then decreasing the pressure on the isolated formation fluid;
- simultaneously as the pressure on the isolated formation fluid is increased utilizing the first pump, utilizing a second pump to pump formation fluid from the probe along a second flowpath, wherein the second flowpath is in an opposite direction from the first flowpath;
- measuring at least one fluid property of the formation fluid of the first flowpath over a time interval as the pressure on the formation fluid in the first flowpath is decreased; and
- determining at least one phase behavior property from the at least one measured fluid property.

18. The method of claim 17, wherein the at least one fluid property measured includes one of pressure, temperature, density, flow rate, composition, optical property, capacitance, resistivity, sonic property, ultrasonic property, chromatographic, and microfluidic.

19. The method of claim 17, wherein the at least one phase behavior property determined is one of fluid fraction, compressibility, viscosity, and gas-oil-ratio (GOR) measurement.

* * * * *